United States Patent
Chen

(10) Patent No.: US 11,328,485 B2
(45) Date of Patent: May 10, 2022

(54) METHOD AND APPARATUS FOR DISPLAYING AN AUGMENTED-REALITY IMAGE CORRESPONDING TO A MICROSCOPE VIEW

(71) Applicant: TENCENT AMERICA LLC, Palo Alto, CA (US)

(72) Inventor: Hanbo Chen, Seattle, WA (US)

(73) Assignee: TENCENT AMERICA LLC, Palo Alto, CA (US)

( * ) Notice: Subject to any disclaimer, the term of this patent is extended or adjusted under 35 U.S.C. 154(b) by 0 days.

(21) Appl. No.: 16/549,073

(22) Filed: Aug. 23, 2019

(65) Prior Publication Data

US 2021/0056759 A1   Feb. 25, 2021

(51) Int. Cl.
| | | |
|---|---|---|
| *G06T 19/00* | (2011.01) | |
| *G02B 21/00* | (2006.01) | |
| *G06F 3/01* | (2006.01) | |
| *G06K 9/00* | (2022.01) | |
| *G02B 21/36* | (2006.01) | |
| *G02B 27/01* | (2006.01) | |

(52) U.S. Cl.
CPC .......... *G06T 19/006* (2013.01); *G02B 21/365* (2013.01); *G02B 27/017* (2013.01); *G06F 3/011* (2013.01); *G06F 3/017* (2013.01); *G06K 9/00671* (2013.01); *G02B 2027/014* (2013.01)

(58) Field of Classification Search
None
See application file for complete search history.

(56) References Cited

U.S. PATENT DOCUMENTS

| | | | | |
|---|---|---|---|---|
| 5,293,574 | A | * 3/1994 | Roehm | A61B 6/504 348/E5.046 |
| 2004/0170309 | A1 | * 9/2004 | Hughes | G06T 7/30 382/128 |
| 2008/0097209 | A1 | * 4/2008 | Lee | G06T 7/12 600/443 |
| 2008/0298660 | A1 | * 12/2008 | Yamagata | A61B 6/032 382/131 |
| 2010/0157041 | A1 | * 6/2010 | Klaiman | A61B 34/10 348/77 |
| 2010/0172556 | A1 | * 7/2010 | Cohen | A61B 6/12 382/128 |

(Continued)

OTHER PUBLICATIONS

GCFLearnFree.org, "PowerPoint: Applying Transitions", Mar. 17, 2016, URL: https://www.youtube.com/watch?v=Ey1atEavZ-M&t=106s (Year: 2016).*

*Primary Examiner* — David H Chu
(74) *Attorney, Agent, or Firm* — Sughrue Mion, PLLC

(57) ABSTRACT

A method of displaying an augmented reality (AR) image includes controlling an AR display to display the AR image as being at least partially overlaid over a view through a microscope while the view is visible to a user of the microscope, wherein the AR image includes a cursor; receiving a user input from a user interface; setting an anchor point based on the user input; updating the AR image to include the anchor point; controlling the AR display to display the updated AR image; detecting a motion of a slide of the microscope; adjusting the AR image by moving at least one from among the cursor and the anchor point within the AR image based on the detected motion; and controlling the AR display to display the adjusted AR image.

21 Claims, 6 Drawing Sheets

(56) References Cited

U.S. PATENT DOCUMENTS

| | | | |
|---|---|---|---|
| 2013/0195339 A1* | 8/2013 | Endo | G06K 9/46 |
| | | | 382/131 |
| 2015/0178969 A1* | 6/2015 | Yoo | G06T 11/60 |
| | | | 345/589 |
| 2015/0228063 A1* | 8/2015 | Minakawa | G06K 9/52 |
| | | | 382/151 |
| 2016/0147408 A1* | 5/2016 | Bevis | G02B 27/017 |
| | | | 715/850 |
| 2016/0358382 A1* | 12/2016 | Lee | H04N 9/31 |
| 2017/0323356 A1* | 11/2017 | Gharabegian | A45B 17/00 |
| 2018/0137689 A1* | 5/2018 | Eastwood | G06T 15/08 |
| 2018/0182171 A1* | 6/2018 | Lipner | G06T 11/00 |
| 2018/0203581 A1* | 7/2018 | Takeda | G06F 3/0488 |
| 2018/0350145 A1* | 12/2018 | Byl | G06F 3/017 |
| 2019/0050999 A1* | 2/2019 | Piat | G06T 15/08 |
| 2019/0134425 A1* | 5/2019 | van Baar | A61N 5/1067 |
| 2019/0258046 A1* | 8/2019 | Gallagher-Gruber | |
| | | | G02B 21/361 |
| 2019/0279380 A1* | 9/2019 | Bendall | G01B 11/24 |
| 2019/0325785 A1* | 10/2019 | Huang | G06T 19/006 |
| 2020/0097727 A1* | 3/2020 | Stumpe | G06T 11/60 |
| 2020/0210704 A1* | 7/2020 | Han | G06T 3/40 |

\* cited by examiner

METHOD AND APPARATUS FOR DISPLAYING AN AUGMENTED-REALITY IMAGE CORRESPONDING TO A MICROSCOPE VIEW

FIELD

The present disclosure is related to augmented reality. Specifically, the present disclosure is related to displaying an augmented-reality image corresponding to a microscope view.

BACKGROUND

Currently, most microscope operators purely rely on their experience to give rough measurement, such as the size of the lesion area or the number of cells. This approach is objective and thus inaccurate.

Some solutions propose taking digital photos from the microscope first and then use computer software to conduct analysis. For instance, CN109029247A and EP2473928B1 propose using software to measure photos taken by special light microscope.

However, to conduct measurement on computer, users need to switch between microscope and computer to operate, which is not efficient and time consuming. As a result, such systems have been rarely adopted by users such as pathologists.

Also, because the measurement is conducted on the screenshot of microscope, the area that can be measured is limited by the field of view under microscope. If the tissue is too large to be fully captured with one screenshot, it cannot be measured by the system.

SUMMARY

According to an embodiment, a method of displaying an augmented reality (AR) image, the method may include controlling an AR display to display the AR image as being at least partially overlaid over a view through a microscope while the view is visible to a user of the microscope, wherein the AR image includes a cursor; receiving a user input from a user interface; setting an anchor point based on the user input; updating the AR image to include the anchor point; controlling the AR display to display the updated AR image; detecting a motion of a slide of the microscope; adjusting the AR image by moving at least one from among the cursor and the anchor point within the AR image based on the detected motion; and controlling the AR display to display the adjusted AR image.

According to an embodiment, a device for displaying an augmented reality (AR) image may include an AR display configured to display an AR image as being at least partially overlaid over a view through a microscope while the view is visible to a user of the microscope; at least one motion sensor configured to detect a motion of a slide of the microscope; a user interface configured to receive a user input; at least one memory configured to store program code; and at least one processor configured to read the program code and operate as instructed by the program code, the program code including: first displaying code configured to cause the at least one processor to control the AR display to display the AR image including a cursor; receiving code configured to cause the at least one processor to receive the user input from the user interface; setting code configured to cause the at least one processor to set an anchor point based on the user input; updating code configured to cause the at least one processor to update the AR image to include the anchor point; second displaying code configured to cause the at least one processor to control the AR display to display the updated AR image; detection code configured to cause the at least one processor to detect the motion of the slide from the motion sensor; adjusting code configured to cause the at least one processor to adjust the AR image by moving at least one from among the cursor and the anchor point within the AR image based on the detected motion; and third displaying code configured to cause the at least one processor to control the AR display to display the adjusted AR image.

According to an embodiment, a non-transitory computer-readable medium may store instructions, the instructions including: one or more instructions that, when executed by one or more processors of a device for displaying an augmented reality (AR) image, cause the one or more processors to: control an AR display to display the AR image as being at least partially overlaid over a view through a microscope while the view is visible to a user of the microscope, wherein the AR image includes a cursor; receive a user input from a user interface; set an anchor point based on the user input; update the AR image to include the anchor point; control the AR display to display the updated AR image; detect a motion of a slide of the microscope; adjust the AR image by moving at least one from among the cursor and the anchor point within the AR image based on the detected motion; and control the AR display to display the adjusted AR image.

DETAILED DESCRIPTION

Augmented reality (AR) may refer to a technology that superimposes a computer-generated image on a user's view of the real world, thus providing a composite view. Embodiments of the present disclosure relate to processes, devices, and systems that may allow users to directly measure objects under a microscope using an AR image overlaid onto a view through the microscope. According to embodiments, a user can plot virtual objects such as a point, line, circle, rectangle, or a region with arbitrary shape directly under microscope. Embodiments may allow a user to generate measurement based on a user's plot, such as the length of a line, the size of a region, the intensity histogram in the region, the type of the region, or the number of objects, for example cells, inside the regions. The virtual objects may also be saved and applied to highlight areas on microscope screenshot.

Embodiments of the present disclosure allow a user to conduct measurement and show the result directly under a microscope. Users may freely move the tissue around during measurement and thus limitations on the field of view may be reduced. Users may also use this system to plot and highlight a region of interest under microscope.

Figure 1:
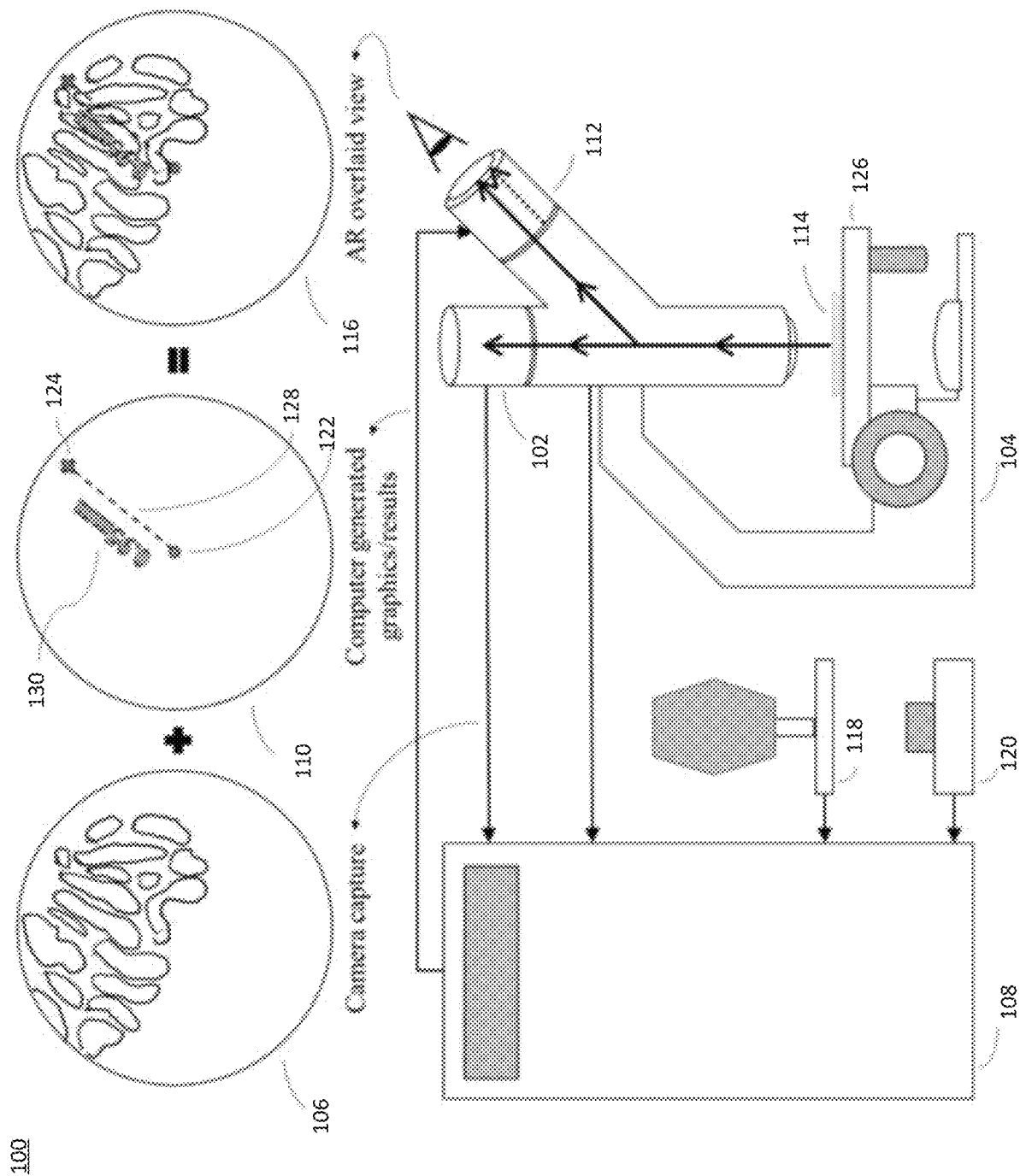
FIG. 1 is a diagram of an overview of an example implementation of an augmented-reality microscope system, according to an embodiment.

FIG. 1 is an illustration of an embodiment of an AR microscope system 100. According to embodiments, AR microscope system 100 may include an image sensor, for example a camera 102, which may capture a microscope image 104 of a view under microscope 106. A computer 108 may compute and generate the graphics, for example an AR image 110, based on the microscope image 104 captured by the camera 102. An AR device 112 may overlay the computer generated AR image 110 with the view under the microscope 104. A user may observe the slide 114 using microscope together with the AR image 110 as AR overlaid view 116. In this way, a large amount of information may be presented through microscope 106. In addition, the user may interact with computer 108 by speech control through microphone 118, or physical input devices including but not limited to button 120, or a keyboard, a mouse, or a paddle.

When conducting measurement, a virtual cursor 122 will be shown as a dot in the center of AR device 108. The user can place anchor points 124 using this virtual cursor 122. The virtual cursor 116 may be similar to, for example, a cursor shown on computer monitor. However, in embodiment, virtual cursor 116 may stay in the middle of the view through microscope 104 while the slide 110 moves. This may be consistent with the operation of microscope 106. In embodiments, slide 110 may be placed on top of the stage 126 and the operator move the stage 126 around to inspect different parts of the slide 110. When moving slide 110, all previous plots such as anchor points 124 may move together with the slide.

In embodiments, AR microscope system 100 may include microscope 104, which may zoom and inspect slide 114. The microscope 104 can send a signal to computer 108 to tell the computer 108 that objective lens of microscope 104 is currently in use when the objective lens is switched on, or the computer 108 send a request signal for the information. AR microscope system 100 may include an image sensor such as digital camera 102, which may be installed on a lens tube of microscope 104 to capture an image 106 of the view under microscope 104. AR microscope system 100 may include an AR device 112 such as an AR lens, which may be installed on an ocular portion of microscope 104 to overlay a virtual screen such as AR image 110 on top of the view of slide. AR microscope system 100 may include computer 108, which may provide image computation and data storage.

According to embodiments, AR microscope system 100 may include Microphone 118, which may be a voice input device for user to control AR microscope system 100. AR microscope system 100 may also include other inputs such as button 120, or a keyboard, mouse, or paddle, which may be physical input devices for user to control the AR microscope system 100.

According to embodiments, AR microscope system 100 may include software and graphical user interfaces. For example, AR microscope system 100 a motion tracking algorithm track the movement of slide 114 under microscope 104. AR microscope system 100 may include a virtual layer, for example a layer shown in AR image 110, that may move together with the slide 110 and record virtual objects such as anchor point 124 plotted by the user. AR microscope system 100 may include virtual cursor 122 placed in the center of the view. AR microscope system 100 may include a user interface that enable users to plot under microscope 104, for example by drawing line 128. AR microscope system 100 may include a user interface that can interactively show the measurement result 130 under microscope 104. AR microscope system 100 may include a storage system that can save images and videos captured by the camera 102. A storage system that can save the virtual plots, for example as shown in AR image 110, which are made by the user. AR microscope system 100 may include a computer software that allows users to load the saved images and videos together with the virtual plots. AR microscope system 100 may include a printing service that can print the captured photos with or without virtual plot overlaid on top of it.

Figure 2A:
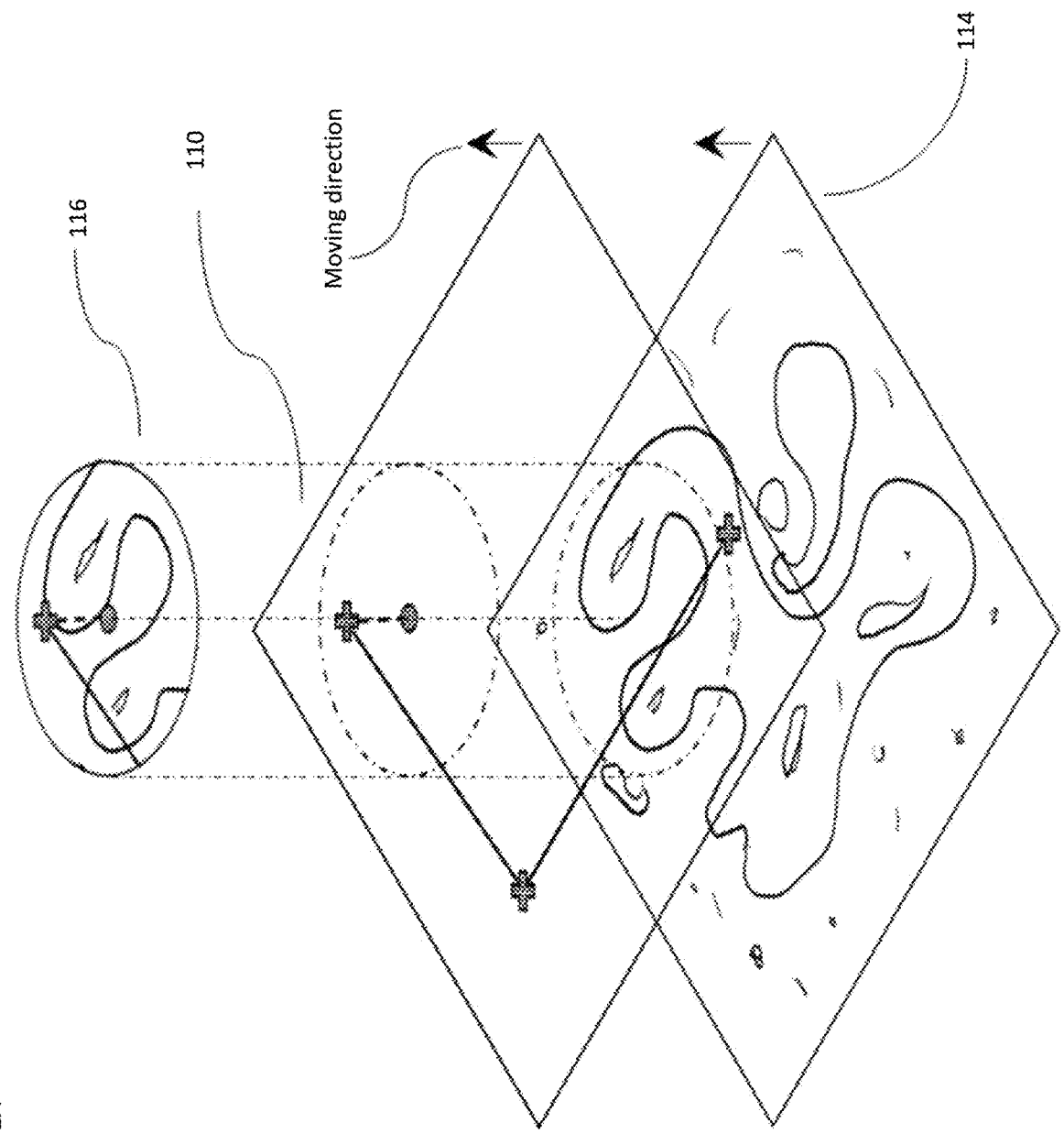
FIGS. 2A-2B are illustrations of a movement of a slide of an augmented-reality microscope system, according to an embodiment.
Figure 2B:
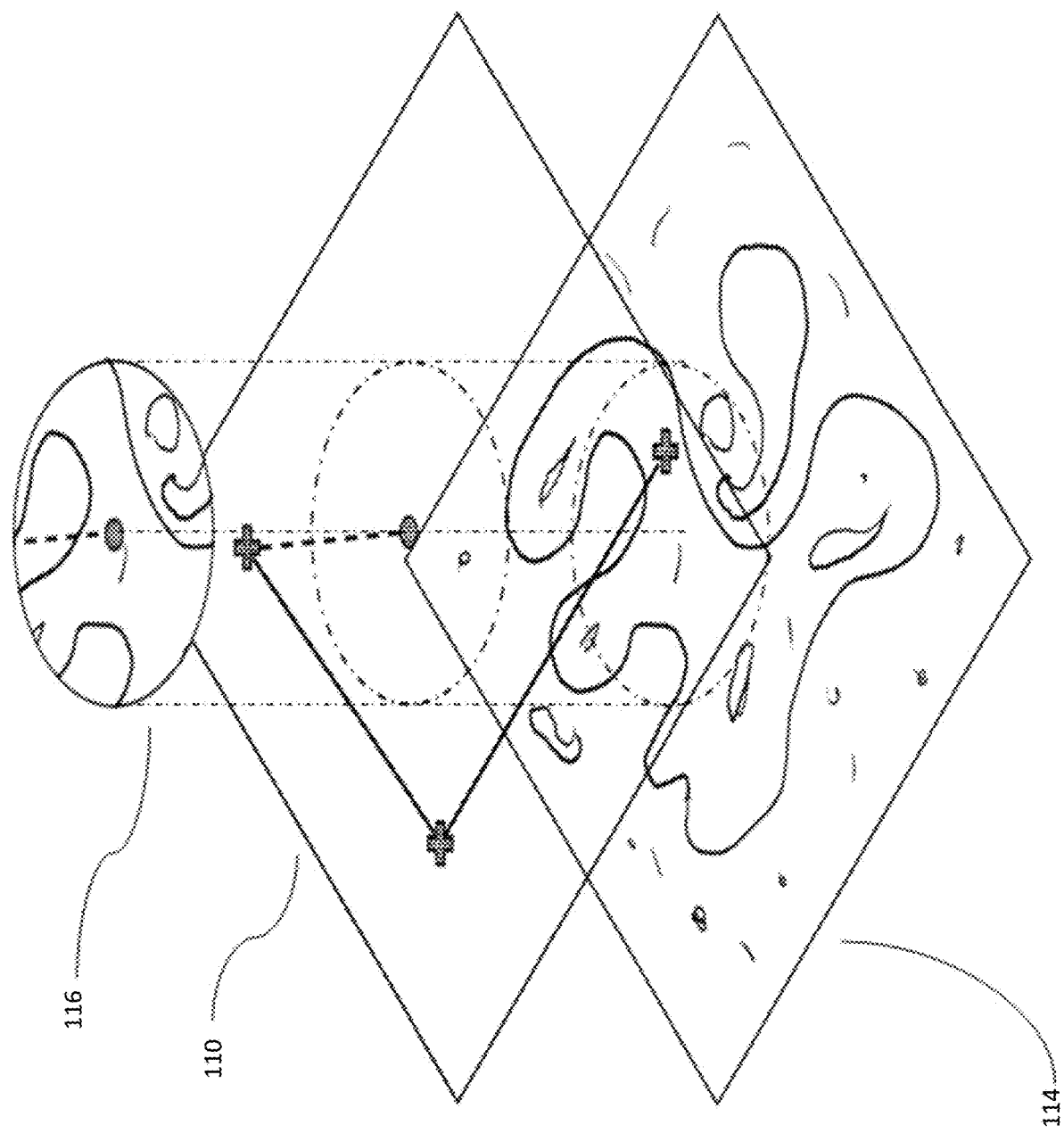

As illustrated in FIGS. 2A-2B, a user can experience the operation of AR microscope system 100 as if there is a virtual screen, for example AR image 110, that moves together with the slide 114. And all the plots, for example anchor point 124 and line 128 may be drawn on the virtual screen. For example, FIG. 2A shows an example of slide 114, AR image 110, and AR overlaid view 116 before a motion of slide 114 in the indicated moving direction, while FIG. 2B shows an example of slide 114, AR image 110, and AR overlaid view 116 are the motion of slide 114 in the indicated moving direction.

According to an embodiment, computer 108 may track a motion of slide 114. For example, camera 102 may record microscope view 106 in a sequence of frames. The frames are passed to computer 108. The computer 108 may compare adjacent frames and detect and compute the shift from the previous frame $F_{t-1}$ to current frame $F_t$.

One possible way to compute such a motion or shift is in following steps:

1) Compute key points $P_{t-1}$ on frame $F_{t-1}$
2) Find the correspondence of $P_{t-1}$ on the current frame: $P_t$
3) Compute the distance between $P_{t-1}$ and $P_t$:

$$\Delta_t = P_t - P_{t-1}$$

4) Shift the virtual screen with $\Delta_t$ and update the graphical plot included in AR image 110 of AR display 112.

In embodiments, the motion tracking algorithm can also been implemented in other ways. For example, the motion tracking algorithm may include an optical flow algorithm or end-to-end deep learning Siamese network or multiple model ensemble for to estimate the motion between two adjacent frames to improve the accuracy. In addition, the motion tracking algorithm may consider the movement across multiple previous frames to improve temporal stability.

According to embodiments, a user may draw a virtual plot such as line 128 on AR image 110. For example, line 128 may include a ruler, an arrow, or any other visual representation as desired. In an embodiment, a user may use speech command (e.g. say "draw a line") or keyboard command (e.g. press key 'l') or press the button 120 with predefined pattern (e.g. single click) to start. When started, AR microscope system 100 may record the current location of virtual cursor 122 by placing anchor points 124 on the virtual screen 110 accordingly. When moving the stage 114, a line 128 may be plotted between the virtual cursor 122 and the anchor point 124. If the user chooses a ruler function, a measurement such as a length of the line may be shown next to the virtual cursor 122. If the user chooses an arrow function, an arrow pointing from virtual cursor 122 to the anchor 124 may be shown. The user can finish and save the plot by speech command (e.g. say "save") or keyboard command (e.g. press key 's') or by pressing the button 120 with a predefined pattern (e.g. double click). The user can finish and delete the plot by speech command (e.g. say "stop") or keyboard command (e.g. press key 'x') or press the button 120 with predefined pattern (e.g. long press).

To conduct measurements, AR microscope system 100 may consider the physical size of pixels of the camera 102 and the object lens. This can be manually set, or can be automatically corrected by a standard grid ruler slide together with an auto-correction program. The grid ruler may be a slide with checker-board like grid plot on it. Each square on the check board may be of fixed size: e.g. 10 micron meter. The auto-correction program may detect those grids and count the number of pixels inside the grids to automatically estimate the physical size of pixels.

According to embodiments, a user may draw a virtual polygon plot on AR image 110. In an embodiment, the user may use speech command (e.g. say "draw a polygon") or keyboard command (e.g. press key 'p') or press the button with predefined pattern (e.g. double click) to start. When started, AR microscope system 100 may record the current location of virtual cursor 122 by placing an anchor points 124 on the virtual screen 110 accordingly. When moving the stage 114, a line 128 may be plotted between the virtual cursor 122 and the anchor point 124. The user can drop a new anchor point in current virtual cursor location by speech command (e.g. say "next") or keyboard command (e.g. press key 'k') or press the button 120 with predefined pattern (e.g. single click). When the user does so, a fixed line may be plotted between the new anchor point and the previous anchor point, and another line may start from the new anchor to the virtual cursor 122. The user may finish and save the plot by speech command (e.g. say "save") or keyboard command (e.g. press key 's') or press the button 120 with predefined pattern (e.g. double click). When the user does so, a line may be plotted between the first cursor and the last cursor to generate a closed polygon. After the user finishes, the area size of the polygon can be shown on the virtual screen 110 next to the polygon. The user can finish and delete the plot by speech command (e.g. say "stop") or keyboard command (e.g. press key 'x') or press the button 120 with predefined pattern (e.g. long press).

According to embodiments, a user may draw a spherical or rectangular plot on AR image 110. n an embodiment, the user may use speech command (e.g. say "draw a sphere") or keyboard command (e.g. press key 'o') or press the button 120 with predefined pattern (e.g. long press) to start. When started, AR microscope system 100 may record the current location of virtual cursor 122 by placing anchor points 124 on the virtual screen 110 accordingly. When moving the stage 114, a sphere may be plotted by taking the anchor point 124 as center and the line 128 between the virtual cursor 122 and the anchor point 124 as radius. If the user chooses a rectangle function, a rectangle may be plotted by taking the line 128 between virtual cursor 122 and the anchor point 124 as diagonal. The user can finish and save the plot by speech command (e.g. say "save") or keyboard command (e.g. press key 's') or press the button 120 with predefined pattern (e.g. double click). The user can finish and delete the plot by speech command (e.g. say "stop") or keyboard command (e.g. press key 'x') or press the button with predefined pattern (e.g. long press).

According to embodiments, a user may take measurements. Measurements, for example measurement 130, can be shown during the plot or after the plot finished. The user may turn measurements on or off, or select the measurement to be displayed by the speech or physical controls. The type of measurements available includes but are not limited to:

1) Length: line length, circle radius, rectangle diagonal
2) Size: area size of an object
3) Color distribution: color mean/std, color histogram, frequency distribution
4) Cell count: the number of cells inside an area
5) Tissue count: the percentage of different type of tissues inside an area Accordingly, AR microscope system 100 may allow the user conduct interactive plots under microscope to high-light and/or measure areas directly under microscope, which the traditional microscope is not capable of. AR microscope system 100 may allow the user to measure objects under microscope even the when the object is too large to be entirely captured under microscope, which current microscope software is not capable of. Further, AR microscope system 100 may allow the user to save and/or print AR images such as plots together with the images captured, which helps record the data for later inspection.

Figure 3:
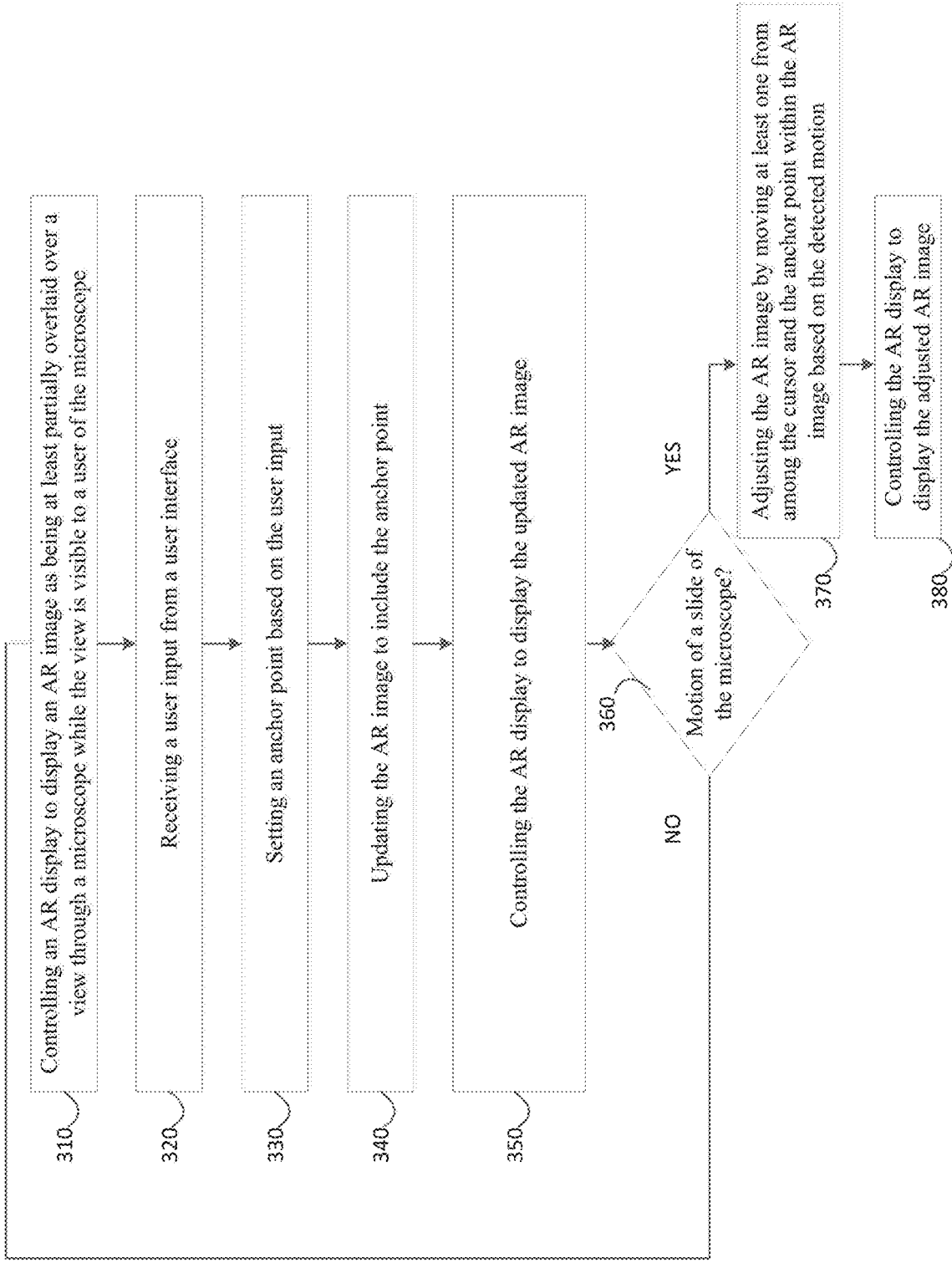
FIG. 3 is a flow chart of an example process for displaying an augmented-reality image.

FIG. 3 is a flow chart of an example process 300 for displaying an augmented reality (AR) image. In some implementations, one or more process blocks of FIG. 3 may be performed by computer 108 or platform 420, described below. In some implementations, one or more process blocks of FIG. 3 may be performed by another device or a group of devices separate from or including computer 108 or platform 420, such as microscope 104, camera 102, AR device 112, or user device 410 described below.

As shown in FIG. 3, process 300 may include controlling an AR display to display the AR image as being at least partially overlaid over a view through a microscope while the view is visible to a user of the microscope, wherein the AR image includes a cursor (block 310).

As further shown in FIG. 3, process 300 may include receiving a user input from a user interface (block 320).

As further shown in FIG. 3, process 300 may include setting an anchor point based on the user input (block 330).

As further shown in FIG. 3, process 300 may include updating the AR image to include the anchor point (block 340).

As further shown in FIG. 3, process 300 may include controlling the AR display to display the updated AR image (block 350).

As further shown in FIG. 3, process 300 may include detecting a motion of a slide of the microscope (block 360).

As further shown in FIG. 3, if there is no motion (block 360—NO), then process 300 may return to block 310.

As further shown in FIG. 3, if motion is detected (block 360—YES), then process 300 may include adjusting the AR image by moving at least one from among the cursor and the anchor point within the AR image based on the detected motion (block 370).

As further shown in FIG. 3, process 300 may include controlling the AR display to display the adjusted AR image (block 380).

According to an embodiment the adjusted AR image may include a line displayed between the anchor point and the cursor.

According to an embodiment, process 300 may further include defining an area within the AR image based on the line.

According to an embodiment the anchor point may be included in a plurality of anchor points, the line may be included in a plurality of lines determined based on the plurality of anchor points, and the area may be bounded by the plurality of lines.

According to an embodiment the area may include a rectangle, and the line may be a diagonal of the rectangle.

According to an embodiment the area may include a circle, the cursor may be located at a center of the circle, the anchor point may be located on a circumference of the circle, and the line may be a radius of the circle.

According to an embodiment the adjusted AR image may include a measurement determined based on the line, wherein the measurement may include at least one from among a length of the line, a size of the area, a color distribution of colors included in the area, a color histogram of the colors included in the area, a frequency distribution of the colors included in the area, a number of cells included in the area, and a percentage of the area that may include a predetermined type of tissue.

According to an embodiment the user input may include at least one from among a button press, a keyboard input, a mouse input, and a voice input.

According to an embodiment process 300 may further include capturing a plurality of image frames of the view through the microscope, wherein a distance of the motion and a direction of the motion may be determined based on a difference between a first point in a first image frame of a plurality of image frames and a second point in a second image frame of the plurality of image frames, the second point corresponding to the first point, and wherein the adjusted AR image may be adjusted based on the determined distance and the determined direction.

According to an embodiment process 300 may further include storing an image comprising the view through the microscope at least partially overlaid with the adjusted AR image.

Although implementations herein describe phoneme sequences, it should be understood that other implementations include word sequences, character sequences, and/or the like, as intermediate sequences. In other words, other implementations include the direct mapping between a speech waveform and word and/or character sequences.

Although FIG. 3 shows example blocks of process 300, in some implementations, process 300 may include additional blocks, fewer blocks, different blocks, or differently arranged blocks than those depicted in FIG. 3. Additionally, or alternatively, two or more of the blocks of process 300 may be performed in parallel.

Figure 4:
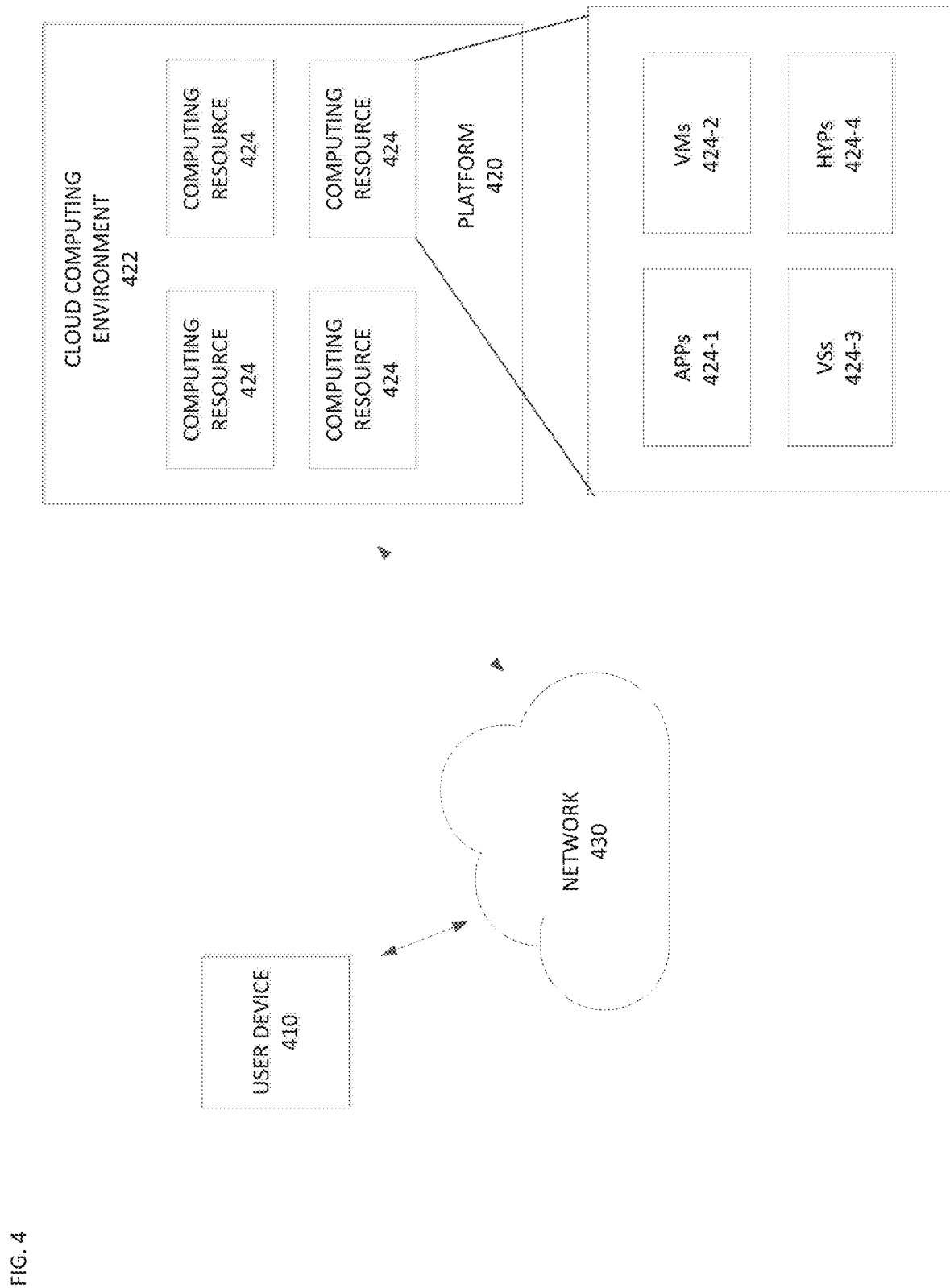
FIG. 4 is a diagram of an example environment in which systems and/or methods, described herein, may be implemented.

FIG. 4 is a diagram of an example environment 400 in which systems and/or methods, described herein, may be implemented. As shown in FIG. 4, environment 400 may include a user device 410, a platform 420, and a network 430. For example, user device 410 may correspond to various components such as microscope 104, camera 102, and AR device 112. In addition, platform 420 may correspond to computer 108. Devices of environment 400 may interconnect via wired connections, wireless connections, or a combination of wired and wireless connections.

User device 410 includes one or more devices capable of receiving, generating, storing, processing, and/or providing information associated with platform 420. For example, user device 410 may include a computing device (e.g., a desktop computer, a laptop computer, a tablet computer, a handheld computer, a smart speaker, a server, etc.), a mobile phone (e.g., a smart phone, a radiotelephone, etc.), a wearable device (e.g., a pair of smart glasses or a smart watch), or a similar device. In some implementations, user device 410 may receive information from and/or transmit information to platform 420.

Platform 420 includes one or more devices capable of generating an AR image to be displayed as overlaid onto a view through a microscope, as described elsewhere herein. In some implementations, platform 420 may include a cloud server or a group of cloud servers. In some implementations, platform 420 may be designed to be modular such that certain software components may be swapped in or out depending on a particular need. As such, platform 420 may be easily and/or quickly reconfigured for different uses.

In some implementations, as shown, platform 420 may be hosted in cloud computing environment 422. Notably, while implementations described herein describe platform 420 as being hosted in cloud computing environment 422, in some implementations, platform 420 is not be cloud-based (i.e., may be implemented outside of a cloud computing environment) or may be partially cloud-based.

Cloud computing environment 422 includes an environment that hosts platform 420. Cloud computing environment 422 may provide computation, software, data access, storage, etc. services that do not require end-user (e.g., user device 410) knowledge of a physical location and configuration of system(s) and/or device(s) that hosts platform 420. As shown, cloud computing environment 422 may include a group of computing resources 424 (referred to collectively as "computing resources 424" and individually as "computing resource 424").

Computing resource 424 includes one or more personal computers, workstation computers, server devices, or other types of computation and/or communication devices. In some implementations, computing resource 424 may host platform 420. The cloud resources may include compute instances executing in computing resource 424, storage devices provided in computing resource 424, data transfer devices provided by computing resource 424, etc. In some implementations, computing resource 424 may communicate with other computing resources 424 via wired connections, wireless connections, or a combination of wired and wireless connections.

As further shown in FIG. 4, computing resource 424 includes a group of cloud resources, such as one or more applications ("APPs") 424-1, one or more virtual machines ("VMs") 424-2, virtualized storage ("VSs") 424-3, one or more hypervisors ("HYPs") 424-4, or the like.

Application 424-1 includes one or more software applications that may be provided to or accessed by user device 410. Application 424-1 may eliminate a need to install and execute the software applications on user device 410. For example, application 424-1 may include software associated with platform 420 and/or any other software capable of being provided via cloud computing environment 422. In some implementations, one application 424-1 may send/receive information to/from one or more other applications 424-1, via virtual machine 424-2.

Virtual machine 424-2 includes a software implementation of a machine (e.g., a computer) that executes programs like a physical machine. Virtual machine 424-2 may be either a system virtual machine or a process virtual machine, depending upon use and degree of correspondence to any real machine by virtual machine 424-2. A system virtual machine may provide a complete system platform that supports execution of a complete operating system ("OS"). A process virtual machine may execute a single program, and may support a single process. In some implementations, virtual machine 424-2 may execute on behalf of a user (e.g., user device 410), and may manage infrastructure of cloud computing environment 422, such as data management, synchronization, or long-duration data transfers.

Virtualized storage 424-3 includes one or more storage systems and/or one or more devices that use virtualization techniques within the storage systems or devices of computing resource 424. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 424-4 may provide hardware virtualization techniques that allow multiple operating systems (e.g., "guest operating systems") to execute concurrently on a host computer, such as computing resource 424. Hypervisor 424-4 may present a virtual operating platform to the guest operating systems, and may manage the execution of the guest operating systems. Multiple instances of a variety of operating systems may share virtualized hardware resources.

Network 430 includes one or more wired and/or wireless networks. For example, network 430 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, or the like, and/or a combination of these or other types of networks.

The number and arrangement of devices and networks shown in FIG. 4 are provided as an example. In practice, there may be additional devices and/or networks, fewer devices and/or networks, different devices and/or networks, or differently arranged devices and/or networks than those shown in FIG. 4. Furthermore, two or more devices shown in FIG. 4 may be implemented within a single device, or a single device shown in FIG. 4 may be implemented as multiple, distributed devices. Additionally, or alternatively, a set of devices (e.g., one or more devices) of environment 200 may perform one or more functions described as being performed by another set of devices of environment 200.

Figure 5:
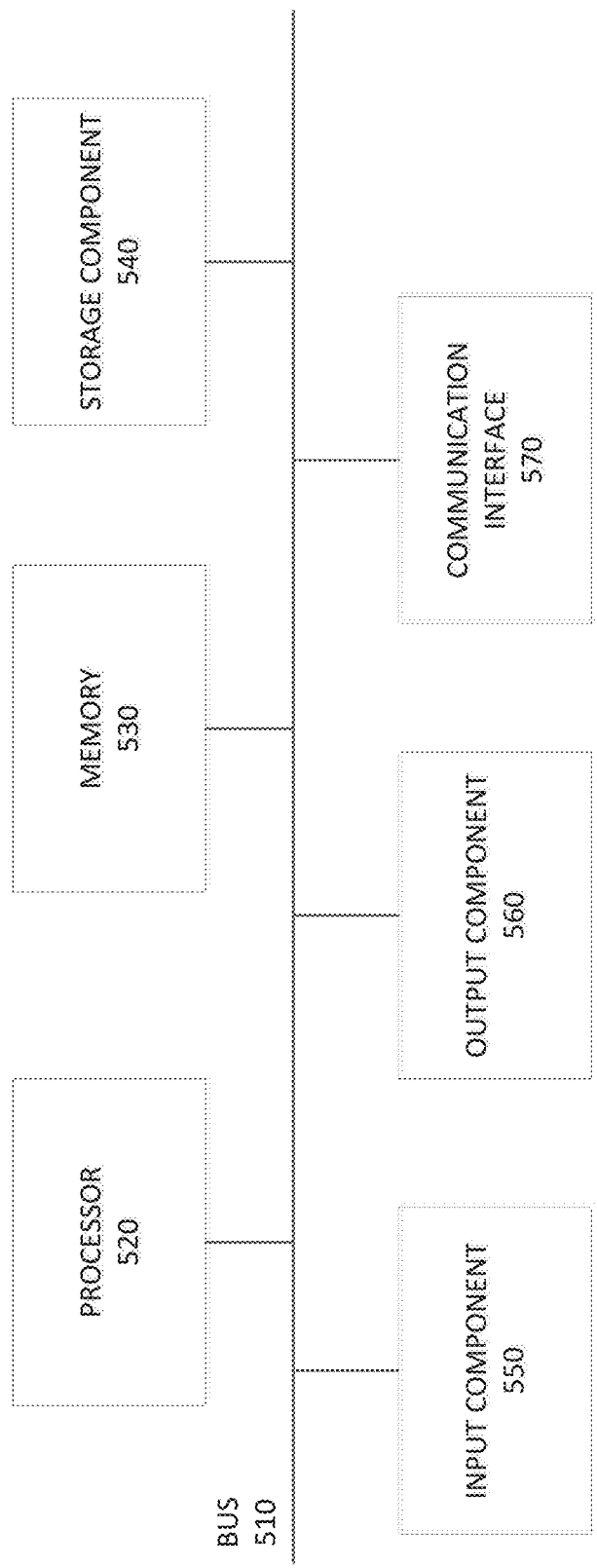
FIG. 5 is a diagram of example components of one or more devices of FIG. 4.

FIG. 5 is a diagram of example components of a device 300. Device 300 may correspond to user device 410 and/or platform 420. As shown in FIG. 5, device 300 may include a bus 510, a processor 520, a memory 330, a storage component 540, an input component 550, an output component 560, and a communication interface 570.

Bus 510 includes a component that permits communication among the components of device 300. Processor 520 is implemented in hardware, firmware, or a combination of hardware and software. Processor 520 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 520 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 520.

Storage component 540 stores information and/or software related to the operation and use of device 300. For example, storage component 540 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 550 includes a component that permits device 300 to receive information, such as via user input (e.g., a touch screen display, a keyboard, a keypad, a mouse, a button, a switch, and/or a microphone). Additionally, or alternatively, input component 550 may include a sensor for sensing information (e.g., a global positioning system (GPS) component, an accelerometer, a gyroscope, and/or an actuator). Output component 560 includes a component that provides output information from device 300 (e.g., a display, a speaker, and/or one or more light-emitting diodes (LEDs)).

Communication interface 570 includes a transceiver-like component (e.g., a transceiver and/or a separate receiver and transmitter) that enables device 300 to communicate with other devices, such as via a wired connection, a wireless connection, or a combination of wired and wireless connections. Communication interface 570 may permit device 300 to receive information from another device and/or provide information to another device. For example, communication interface 570 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 520 executing software instructions stored by a non-transitory computer-readable medium, such as memory 330 and/or storage component 540. A computer-readable medium is defined herein as a non-transitory memory device. A memory device includes memory space within a single physical storage device or memory space spread across multiple physical storage devices.

Software instructions may be read into memory 330 and/or storage component 540 from another computer-readable medium or from another device via communication interface 570. When executed, software instructions stored in memory 330 and/or storage component 540 may cause processor 520 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 5 are provided as an example. In practice, device 300 may include additional components, fewer components, different components, or differently arranged components than those shown in FIG. 5. Additionally, or alternatively, a set of components (e.g., one or more components) of device 300 may perform one or more functions described as being performed by another set of components of device 300.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method of displaying an augmented reality (AR) image, the method comprising:
   controlling an AR display to display the AR image as being at least partially overlaid over a view through a microscope while the view is visible to a user of the microscope, wherein the AR image includes a cursor;
   receiving a user input from a user interface;
   setting an anchor point based on the user input;
   updating the AR image to include the anchor point;
   controlling the AR display to display the updated AR image;
   detecting a physical motion of a slide included in the microscope;
   adjusting the AR image by moving the anchor point within the AR image based on the physical motion; and
   controlling the AR display to display the adjusted AR image,
   wherein the cursor remains in a center of the view through the microscope during the physical motion of the slide.

2. The method of claim 1, wherein the adjusted AR image comprises a line displayed between the anchor point and the cursor.

3. The method of claim 2, further comprising defining an area within the AR image based on the line.

4. The method of claim 3, wherein the anchor point is included in a plurality of anchor points,
   wherein the line is included in a plurality of lines determined based on the plurality of anchor points, and
   wherein the area is bounded by the plurality of lines.

5. The method of claim 3, wherein the area comprises a rectangle, and
   wherein the line is a diagonal of the rectangle.

6. The method of claim 3, wherein the area comprises a circle,
   wherein the cursor is located at a center of the circle,
   wherein the anchor point is located on a circumference of the circle, and
   wherein the line is a radius of the circle.

7. The method of claim 3, wherein the adjusted AR image comprises a measurement determined based on the line,
   wherein the measurement comprises at least one from among a length of the line, a size of the area, a color distribution of colors included in the area, a color histogram of the colors included in the area, a frequency distribution of the colors included in the area, a number of cells included in the area, and a percentage of the area that includes a predetermined type of tissue.

8. The method of claim 1, wherein the user input comprises at least one from among a button press, a keyboard input, a mouse input, and a voice input.

9. The method of claim 1, further comprising capturing a plurality of image frames of the view through the microscope,
   wherein a distance of the motion and a direction of the motion are determined based on a difference between a first point in a first image frame of the plurality of image frames and a second point in a second image frame of the plurality of image frames, the second point corresponding to the first point, and
   wherein the adjusted AR image is adjusted based on the determined distance and the determined direction.

10. The method of claim 1, further comprising storing an image comprising the view through the microscope at least partially overlaid with the adjusted AR image.

11. The method of claim 1, wherein, during the physical motion of the slide, an object included in the slide moves with respect to the cursor while the cursor remains in the center of the view through the microscope.

12. A device for displaying an augmented reality (AR) image, the device comprising:
   an AR display configured to display an AR image as being at least partially overlaid over a view through a microscope while the view is visible to a user of the microscope;
   at least one motion sensor configured to detect a physical motion of a slide of included in the microscope;
   a user interface configured to receive a user input;
   at least one memory configured to store program code; and
   at least one processor configured to read the program code and operate as instructed by the program code, the program code including:
      first displaying code configured to cause the at least one processor to control the AR display to display the AR image including a cursor;
      receiving code configured to cause the at least one processor to receive the user input from the user interface;
      setting code configured to cause the at least one processor to set an anchor point based on the user input;
      updating code configured to cause the at least one processor to update the AR image to include the anchor point;
      second displaying code configured to cause the at least one processor to control the AR display to display the updated AR image;
      detection code configured to cause the at least one processor to detect the physical motion of the slide from the at least one motion sensor;

adjusting code configured to cause the at least one processor to adjust the AR image by moving the anchor point within the AR image based on the detected motion; and third displaying code configured to cause the at least one processor to control the AR display to display the adjusted AR image, wherein the cursor remains in a center of the view through the microscope during the physical motion of the slide.

13. The device of claim 12, wherein the adjusted AR image comprises a line displayed between the anchor point and the cursor.

14. The device of claim 13, wherein the program code further comprises defining code configured to cause the at least one processor to define an area within the AR image based on the line.

15. The device of claim 14, wherein the anchor point is included in a plurality of anchor points, wherein the line is included in a plurality of lines determined based on the plurality of anchor points, and wherein the area is bounded by the plurality of lines.

16. The device of claim 14, wherein the area comprises a rectangle, and wherein the line is a diagonal of the rectangle.

17. The device of claim 14, wherein the area comprises a circle, wherein the cursor is located at a center of the circle, wherein the anchor point is located on a circumference of the circle, and wherein the line is a radius of the circle.

18. The device of claim 14, wherein the adjusted AR image comprises a measurement determined based on the line, wherein the measurement comprises at least one from among a length of the line, a size of the area, a color distribution of colors included in the area, a color histogram of the colors included in the area, a frequency distribution of the colors included in the area, a number of cells included in the area, and a percentage of the area that includes a predetermined type of tissue.

19. The device of claim 12, wherein the at least one motion sensor comprises at least one image sensor configured to capture a plurality of image frames of the view through the microscope, wherein a distance of the motion and a direction of the motion are determined based on a difference between a first point in a first image frame of the plurality of image frames and a second point in a second image frame of the plurality of image frames, the second point corresponding to the first point, and wherein the adjusted AR image is adjusted based on the determined distance and the determined direction.

20. The device of claim 12, wherein the program code further comprises storing code configured to cause the at least one processor to store an image comprising the view through the microscope at least partially overlaid with the adjusted AR image.

21. A non-transitory computer-readable medium storing instructions, the instructions comprising: one or more instructions that, when executed by one or more processors of a device for displaying an augmented reality (AR) image, cause the one or more processors to:

control an AR display to display the AR image as being at least partially overlaid over a view through a microscope while the view is visible to a user of the microscope, wherein the AR image includes a cursor;

receive a user input from a user interface;

set an anchor point based on the user input;

update the AR image to include the anchor point;

control the AR display to display the updated AR image;

detect a physical motion of a slide included in the microscope;

adjust the AR image by moving the anchor point within the AR image based on the detected motion; and control the AR display to display the adjusted AR image, wherein the cursor remains in a center of the view through the microscope during the motion of the slide.

* * * * *